(12) United States Patent
Chuang et al.

(10) Patent No.: US 7,875,751 B2
(45) Date of Patent: Jan. 25, 2011

(54) METHOD FOR THE PURIFICATION OF CAROTENOIDS FROM PLANT EXTRACTS AND THE PRODUCTS SO OBTAINED

(75) Inventors: Chia-Line Chuang, Taipei (TW); Hsin-Ke Li, Taipei (TW); Chong-Nan Chuang, Taipei (TW)

(73) Assignee: Allied Biotech Corporation (TW)

( * ) Notice: Subject to any disclaimer, the term of this patent is extended or adjusted under 35 U.S.C. 154(b) by 120 days.

(21) Appl. No.: 12/289,934

(22) Filed: Nov. 7, 2008

(65) Prior Publication Data

US 2010/0121112 A1   May 13, 2010

(51) Int. Cl.
*C07C 35/21* (2006.01)

(52) U.S. Cl. ........................... 568/823; 568/824

(58) Field of Classification Search .......... None
See application file for complete search history.

(56) References Cited

U.S. PATENT DOCUMENTS

| 5,648,564 | A  | * | 7/1997 | Ausich et al. ............ 568/834 |
| 2005/0139145 | A1 | * | 6/2005 | Quesnel ........................ 117/2 |
| 2007/0161826 | A1 | * | 7/2007 | Pena ........................ 568/824 |

OTHER PUBLICATIONS

Database CAPLUS on STN, Acc. No. 2008:326505, Chen, CN 101139312 (Mar. 12, 2008) (abstract).*

* cited by examiner

*Primary Examiner*—Brian J Davis
(74) *Attorney, Agent, or Firm*—Bacon & Thomas, PLLC

(57) ABSTRACT

A novel process for the preparation of highly purified carotenoids from plant extracts, especially the marigold flower extracts, is disclosed. The process includes the formation, isolation and purification of carotenoids, primarily lutein and zeaxanthin, at lower temperatures with the use of at least a polar solvent and at least a non-polar solvent. The highly purified carotenoids so obtained are useful for human consumption, such as nutritional supplements and pharmaceuticals.

27 Claims, 1 Drawing Sheet

METHOD FOR THE PURIFICATION OF CAROTENOIDS FROM PLANT EXTRACTS AND THE PRODUCTS SO OBTAINED

FIELD OF THE INVENTION

The present invention relates to a process for forming, isolating and purifying carotenoids, more particularly to a process for saponification, separation and purification of lutein and zeaxanthin containing crystals from plant extracts. A simplified and more environmentally friendly process resulting in high purity products is disclosed in this invention.

BACKGROUND OF THE INVENTION

The lutein is one kind of the oxy-carotenoids (called the xanthophylls) and is abundant in fruits and green vegetables, such as broccoli, Brussels sprouts, cabbage, kale, spinach, green beans, lima beans and lettuce, and in flowers, such as the marigold flower. Similar to other carotenoids, the lutein has been studied extensively as an antioxidant for the prevention of cancer and for other health benefits. Medical researches show that lutein and zeaxanthin reduce the age-related macular degeneration of the human body. (See, e.g., Seddon et al., *J. Amer. Med. Assoc.,* 272 (18): 1439-1441, 1994.) The lutein has strong antioxidant capabilities in the human body and the macular degeneration prevention effects of lutein have made it a popular nutritional supplements and pharmaceuticals. Therefore, the FDA also considers lutein as a pharmaceutical. According to the standard requirement of the 30$^{th}$ ed. United States Pharmacopeia, to be qualified as a pharmaceutical the total carotenoids content of a product shall not be less than 80%, with the lutein content of not less than 74% and the zeaxanthin content of not more than 8.5%.

Many researchers have reported the process for the saponification, separation and purification of lutein from marigold flower extracts. The petal of the marigold flower is one of the excellent sources of lutein that exists naturally in the esterified form, as esterified with fatty acids such as the palmitic acids, the lauric acids and the myristic acids. In the conventional art, to produce the lutein crystals from the petals of the marigold flower, at first the marigold flower petals are extracted to obtain an oleoresin, with the n-hexane as the extract solvent. In general, the oleoresin so obtained contains only about 5% to 30% lutein ester. The oleoresin needs to be saponified, separated and recrystalized to obtain the lutein crystals. Usually, the process includes mixing the oleoresin with an alcohol solvent, followed by adding an aqueous or alcoholic solution of alkali into the solution. Thereafter, the solution is maintained at high temperatures until the oleoresin is completely saponified. After the saponification, the solution is diluted in a great amount of deionized water. The diluted solution is then separated in a high-speed centrifugation process using a centrifuge. Collect the solid so obtained and rinse the solid in deionized water and organic solvents to purify. Wet lutein crystals are obtained and are dried in a vacuum environment to obtain the dry crystals of lutein.

Several approaches in the purification of the carotenoids from plant extracts have been disclosed. Khachik (U.S. Pat. No. 5,382,714) disclosed a process for obtaining lutein and zeaxanthin from the marigold oleoresin. Here, the marigold oleoresin is mixed with a 45% aqueous solution of potassium hydroxide and saponified at 65° to 70° C. for about a half hour. The resulted crude lutein was about 70% pure is measured by a spectrophotometer. The crude lutein is then purified in a solvent containing dichloromethane and hexane to obtain lutein crystals of 97% purity. The disadvantages of this approach include that fact that the dichloromethane used in the purification process would reside in the resulted products.

Ausich (U.S. Pat. No. 5,648,564) developed a process for obtaining lutein crystal compositions containing approximately 79% total carotenoids and 73.6% pure lutein. In this invention, the marigold oleoresin is first mixed with 1,2-propanediol and saponified in a 45% alcoholic solution of potassium hydroxide at 70° C. for 10 hours. The saponified oleoresin is diluted in deionized water. Thereafter the lutein crystals so obtained are collected by using a centrifuge and washed in deionized water at 85° C. The drawbacks of this invention include: Saponifying the marigold oleoresin a high temperature for a long period of time would decompose the lutein. The high-speed centrifugation process is costly and increases the separation costs. In addition, the total carotenoids content and lutein content obtained are only 79% and 73.6%, respectively.

Rodriguez (U.S. Pat. No. 6,329,557) disclosed a process in which the saponified oleoresin is dispersed in water, adjusting the pH value of the suspension to 6 with phosphoric acid or acetic acid and maintaining the temperature of the suspension at 60 to 70° C. for 20 to 30 minutes. After that, the oily material is washed three or more times with an acid aqueous solution in organic solvents, such as hexane and heptane. The crystals are collected by filtration and centrifugation. This invention, however, uses a great amount of water and organic solvents and is hazardous to the environmental.

Madhavi (U.S. Pat. No. 6,380,442) mixed marigold oleoresin with iso-propanol and heated the mixture to 60° C. to obtain a free-flowing solution. After that, potassium hydroxide is added and the composition is maintained at the temperature of 60° to 65° C. for 90 minutes to saponify. The saponified oleoresin was diluted in deionized water. After the centrifugation of the solution, fine crystals are collected. The resulted composition has the total carotenoids and lutein contents of 95% and 90%, respectively. Like in the case of the Ausich invention, the disadvantages of this invention are that the high temperature in the saponification would decompose the lutein and that the high-speed centrifugation process in separating the crystals increases the costs of the process.

Kumar (U.S. Pat. No. 6,743,953) used iso-propanol as the solvent to saponify the marigold oleoresin at 70° C. for 3 hours. After that, the iso-propanol solvent is distilled off and the solids are collected, mixed in water by stirring and extracted three times using ethyl acetate. The ethyl acetate in the collected solution is then washed with water and distilled off. Finally, the residual solid is purified with hexane/acetone solution and washed with methanol. The total carotenoids content of the products is 86.23%, as determined by a UV/Vis spectrophotometer, and the total lutein content is 91.43%, as determined by HPLC analysis. Although this method produces highly purified lutein, the process is complicated and time consuming and requires large quantity of solvents and energy.

Recently in the U.S. Pat. No. 7,271,298, Xu proposed a process to improve the purity and the yield rates of the xanthophylls crystal. However, the disadvantages of this process are that the process is performed under high temperatures and that the high-speed centrifugation is required.

In most conventional arts, the main disadvantages are: The process is conducted under higher temperatures, which tend to decompose the lutein. The high-speed centrifugation is required, resulted at higher costs of the process.

It is thus necessary to develop a simplified method for the purification of carotenoids from plant extracts.

It is also necessary to provide an inexpensive method for the purification of carotenoids from plant extracts.

It is also necessary to provide a new method for the purification of carotenoids from plant extracts to obtain higher carotenoids contents.

It is also necessary to provide a method for the purification of carotenoids from plant extracts, wherein the solvents used are environmental.

It is also necessary to provide a method for the purification of carotenoids from plant extracts, wherein the process may be conducted under relatively low temperatures.

It is also necessary to provide a method for the purification of carotenoids from plant extracts, wherein the high-speed centrifugation process is not needed.

OBJECTIVES OF THE INVENTION

The objective of this invention is to provide a novel method for the purification of carotenoids from plant extracts.

Another objective of this invention is to provide a simplified method for the purification of carotenoids from plant extracts.

Another objective of this invention is to provide an inexpensive method for the purification of carotenoids from plant extracts.

Another objective of this invention is to provide a new method for the purification of carotenoids from plant extracts to obtain higher carotenoids contents.

Another objective of this invention is to provide a method for the purification of carotenoids from plant extracts, wherein the solvents used are environmental.

Another objective of this invention is to provide a method for the purification of carotenoids from plant extracts, wherein the process may be conducted under relatively low temperatures.

Another objective of this invention is to provide a method for the purification of carotenoids from plant extracts, wherein the high-speed centrifugation process is not needed.

SUMMARY OF THE INVENTION

The present invention provides a simplified and low-cost method of forming, isolating and purifying carotenoids from plant extracts. In the embodiments of the present invention, a composition containing the lutein and the zeaxanthin crystals are obtained from the marigold oleoresin. The invented method comprises the steps of:
(a) Saponify a carotenoids-containing plant extract in a saponification solution containing at least one polar solvent and at least one nonpolar solvent;
(b) Isolate the saponified products to obtain carotenoids crystals; and
(c) Purify the crystals to obtain highly purified carotenoids.

The carotenoids-containing plant extract is at least one selected from the group consisted of the extract of broccoli, Brussels sprouts, cabbage, kale, spinach, green beans, lima beans and lettuce, and the marigold flower. The marigold flower extract is one of the preferred examples.

The saponification solution may further contain an alkali. The alkali may be potassium hydroxide or sodium hydroxide. The polar solvent may be an alcohol. Examples of the alcohols include methanol, ethanol and propan-2-ol, in which methanol is preferable. The nonpolar solvent may be the aliphatic hydrocarbon solvents, such as hexane, pentane and heptane, while hexane is preferable. The volume ratio of the polar solvent to the nonpolar solvent can be from 1:3 to 3:1. If the alkali is used, the weight ratio of the alkali to the carotenoids-containing plant extract may be from about 0.3 to about 2.0, preferably 1.0 to 1.3. The saponification temperature may be in the range of from 10° C. to about 65° C., preferably from 35° to 40° C.

The invented process may further optionally comprise the step of separating the saponified products to obtain the parts of the saponified products that contains higher concentration of the carotenoids. The invented method may further comprise diluting the saponified products in deionized water before isolating the carotenoids crystals from the saponified products. The carotenoids crystals may be isolated from the saponified products by filtration. The purification may be conducted by drying the wet crystals by heating, freezing or in vacuum, or their combinations. In the preferred embodiments the wet crystals are purified by heating the wet crystals in the temperature of 50° to 100° C. under vacuum for over 2 hours. Washing the crystals with deionized water after isolating the crystals from the solvents is recommendable.

The method may further comprise the steps of solving the carotenoids-containing crystals in a water miscible solvent, removing parts of the solvent at reduced pressure, adding deionized water to recrystallize and filtering the solution to obtain the recrystallized carotenoids-containing crystals, before the purification process. The water miscible solvent may be alcohol, ester or ketone. Preferred examples of the water miscible solvent are propan-2-ol, propan-1,2-diol, ethanol, ethyl acetate and acetone. About 30% to 80% of the solvent is removed before adding the deionized water.

These and other objectives and advantages of the present invention may be clearly understood from the detailed descriptions by referring to the drawings.

DETAILED DESCRIPTIONS OF THE INVENTION

Figure 1:
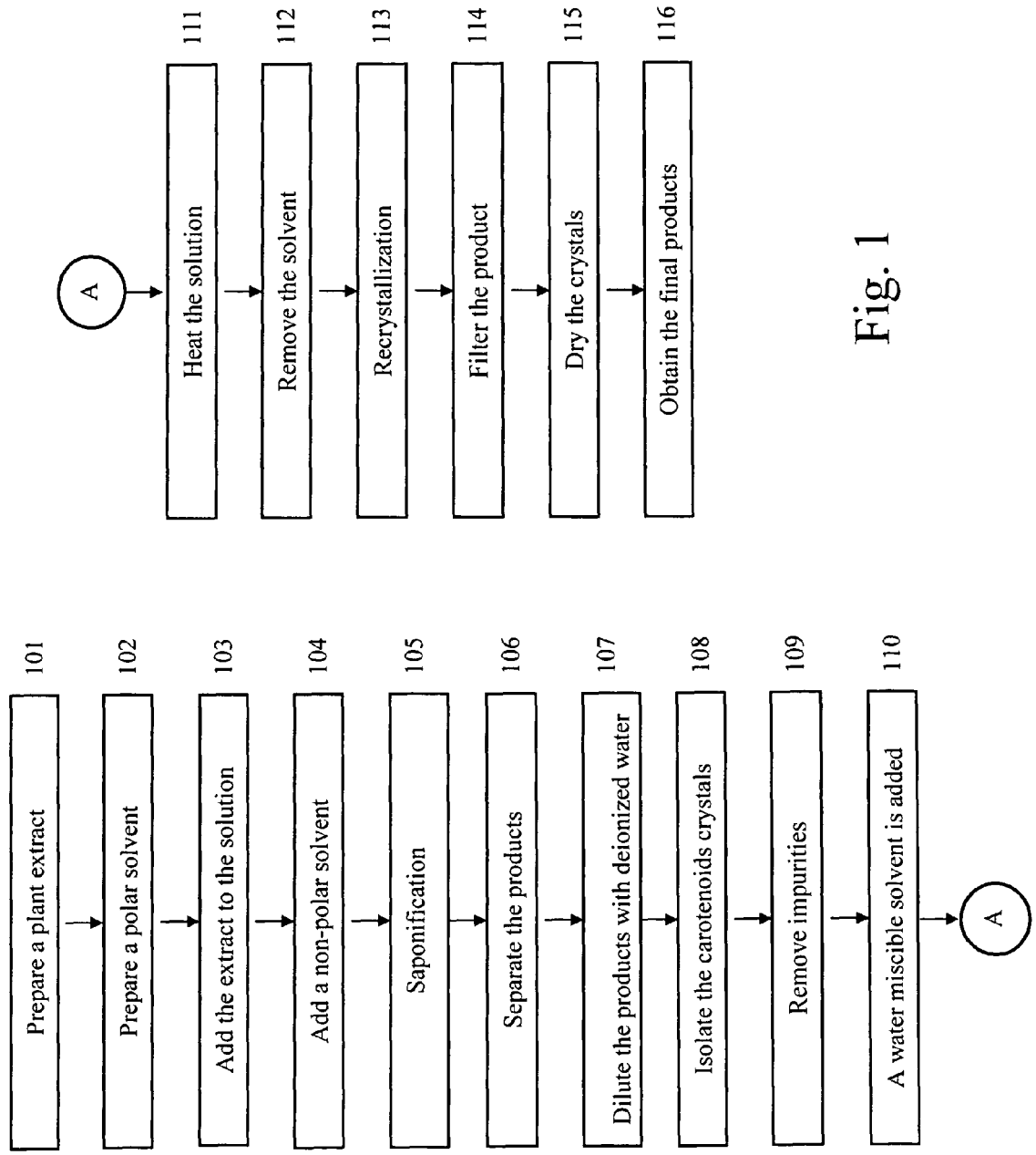
FIG. 1 is the flowchart of one example of the invented method for purification of carotenoids from plant extracts.

The present invention provides a simplified and low-cost method of forming, isolating and purifying carotenoids from plant extracts. In the embodiments of the present invention, a composition containing the lutein and the zeaxanthin crystals are obtained from the marigold oleoresin. The invented method comprises the steps of:
(a) Saponify a carotenoids-containing plant extract in a saponification solution containing at least one polar solvent and at least one nonpolar solvent;
(b) Isolate the products to obtain carotenoids crystals; and
(c) Purify the crystals to obtain highly purified carotenoids.

In the present invention, the carotenoids-containing plant extract may be any plant extract that contain carotenoids. It may be the extract of any plant that contains carotenoids. Examples of the plant are: Fruits and green vegetables, such as broccoli, Brussels sprouts, cabbage, kale, spinach, green beans, lima beans and lettuce, and flowers, such as the marigold flower. The plant extract may be the extract of one or more than one of the carotenoids-containing plants. Additives may also exist in the plant extract. The plant extract is preferably of higher lutein contain. The marigold flower extract is one of the preferred examples and is used in all the embodiments in this invention.

In the invented method, the saponification solution may further contain an alkali. Any alkali may be used in this invention. Examples of the alkali that may be used in this invention include potassium hydroxide and sodium hydroxide. In the preferred embodiments of the invention, the alkali is potassium hydroxide. In this invention, the polar solvent is not limited to any particular type of the polar solvents. Alcohols are preferable but are not any limitation of this invention. Suited alcohols include methanol, ethanol and propan-2-ol. Among them, methanol is most preferable. One or more polar solvents may be used separately or in combination. In the invention, the nonpolar solvent is also not limited to any particular type. In the preferred embodiments, the aliphatic hydrocarbon solvent is used as the nonpolar solvent. Suited aliphatic hydrocarbon solvents are hexane, pentane and heptane, while hexane is most preferable. One or more nonpolar solvents may be used separately or in combination. In the invention, the volume ratio of the polar solvent to the nonpolar solvent can be from 1:3 to 3:1. If the alkali is used, the weight ratio of the alkali to the carotenoids-containing plant extract may be from about 0.3 to about 2.0, preferably 1.0 to 1.3. These, however, are not any technical limitations of the present invention. The saponification temperature may be in the range of from 10° C. to about 65° C., i.e., the boiling temperature of the saponification composition, preferably from 35° to 40° C. Sapponifying the carotenoids-containing plant extract under the temperature of below 10° C. or above 65° C. is acceptable. However, reactions conducted below 10° C. would require a cooling system and would increase the process costs. On the other hand, to process above the boiling temperature of the composition does not only require a heating system but also make the reaction system complicated.

The invented process may further comprise the step of separating the saponified products to obtain the parts of the saponified products that contains higher concentration of the carotenoids. This step, however, is optional, since the impurities contained in the saponified products may be easily removed in the following purification step.

The invented method may further comprise diluting the saponified products with deionized water before isolating the carotenoids crystals from the saponified products. The isolation process may be any method that is able to isolate the carotenoids crystals from the saponified products. Suited methods include the filtration. Other methods that are currently used in the industry are also applicable. The purification of the crystals is not limited to any particular method. Any method that separates the crystals from the solvents and the impurities may be used. In the embodiments of the present invention, the purification is conducted by drying the wet crystals by heating, freezing or in vacuum, or their combinations. In the preferred embodiments the wet crystals are purified by heating the wet crystals in the temperature of 50° to 100° C. under vacuum for over 2 hours. Washing the crystals with deionized water after isolating the crystals from the solvents is recommendable.

In addition, in order to remove the hazardous residual solvents from the carotenoids-containing crystals, the steps of solving the carotenoids-containing crystals in a water miscible solvent, removing parts of the solvent at reduced pressure, adding deionized water to recrystallize and filtering the solution to obtain the recrystallized carotenoids-containing crystals, before the purification process, may be added. The water miscible solvent is not limited to any particular material. It may be alcohol, ester or ketone or any other water miscible solvent. Preferred examples of the water miscible solvent are propan-2-ol, propan-1,2-diol, ethanol, ethyl acetate and acetone. In the embodiments of the present invention, in this step, about 30% to 80% of the solvent is removed before adding the deionized water.

The present invention provides a method for the preparation of highly purified carotenoids crystals with more than 99% total carotenoids contain, more than 92% trans-lutein contain and less than 6% zeaxanthin contain, respectively.

In the present invention, the commercially available marigold oleoresin can be used as the material of the carotenoids-containing plant extract. Such plant extracts are obtained by extracting marigold flower petals using hexane. In general, the oleoresin contains about 5% to 30% lutein esters, more often 8% to 10% lutein esters, and is used as the starting material for producing the highly pure carotenoids in this invention.

Under the current known arts, the saponification process is started by adding the oleoresin in an alcohol, such as ethanol, iso-propanol and propan-1,2-diol. Because the oleoresin cannot mix homogenously with alcohol at the room temperature, the solution is heated and maintained at 60° to 80° C. during the whole saponification process. Lutein is an antioxidant that is sensitive to the environment, such as light, oxygen and heat, and high saponification temperature is great disadvantage. Although it is not intended to limit the scope of the present invention, in the invented method a non-polar solvent is used to solve this problem. It has been found that the non-polar solvent does not only decrease the operating temperature of the saponification process but also increase the quality of the crystals so produced.

As described above, in the conventional art the separation and the purification of the saponified oleoresin require diluting the saponified oleoresin in a great amount of deionized water and collecting the crystals by the high-speed centrifugation. The additional water brings higher loadings to the centrifuge and makes the reuse of the filtrate almost impossible. Nevertheless, the collected crystals are purified by using the organic solvents and/or washed in a great amount of water at high temperature. Contrary to the conventional art, the new invention shows that the carotenoids crystals can be collected by a simple filtration process and is washed in a small amount of water.

In the embodiments of the present invention, the free lutein crystals are collected from the saponified oleoresin by a simple suction filtration process and washed with deionized water at room temperature until the filtrate turns to be clear and chemically neutral.

In the embodiments of this invention, the wet lutein crystals are purified by removing the residual solvents in a vacuum system. In the drying process, the solvents are evaporated in vacuum. To remove the hazardous solvents that may reside in the lutein crystals, such as n-hexane, a simple solvent replacement process is provided before the vacuum drying process. In this process a less hazardous and water miscible solvent is used. In this solvent replacement process, the wet crystals are first dissolved in a suitable low hazardous alcohol, ester or ketone organic solvent, such as propan-2-ol, propan-1,2-diol, ethyl acetate or acetone. After this, the residual hazardous solvents such as n-hexane may be easily removed by a reduced pressure operation. The steps end at recrystallizing the lutein crystals by adding water to the solution.

In the invention, both the methanol and the n-hexane are high vapor pressure solvents. The methanol and the n-hexane collected after the filtration process may be reused after a simple reduced pressure distillation process. Their recovery ratio is more than 70% to 80%. As shown in Example 1 of the Embodiments, the recovered solvents are reused and the same qualities of carotenoids are obtained. This demonstrates that the recovered solvents can be reused.

Embodiments

In the following, several examples will be shown and described to illustrate the method for the purification of carotenoids from plant extracts of the present invention and the products so obtained. It shall be noted that the detailed description of the embodiments is for illustration purpose only and shall not be interpreted as the limitations of the present invention.

FIG. 1 shows the flowchart of an embodiment of the method for the purification of carotenoids from plant extracts of the present invention. As shown in the figure, in the purification of carotenoids from plant extracts, at 101 a carotenoids-containing plant extract is prepared. In this example, the plant extract is the extract oleoresin of the marigold petals. At 102 potassium hydroxide is dissolved in a polar solvent. In this example, the polar solvent is methanol. At 103 the oleoresin is added to the solution, which is kept at the temperature of about 40° C. After that, at 104 a nonpolar alkane solvent, such as n-hexane, is added to modify the composition. At 105 the saponification process is performed at from 10° C. to the boiling temperature of the alcoholic mixture (about 65° C.) for about 1 to 4 hours. The lower saponification temperature prevents the free lutein from decomposition at higher temperature. The length of the saponification period is relative to the saponification temperature.

At 106 the saponification products are separated from the saponified crude mixture solution. At 107 the saponification products are diluted with deionized water and are subjected to filtration at 108 to obtain carotenoids crystals. At 109 the carotenoids crystals are washed with deionized water to remove impurities. At 110 the wet crystals are added to a water miscible solvent. In this example the solvent is propan-2-ol, propan-1,2-diol, ethanol, ethyl acetate or acetone. At 111 provide heat to dissolve the crystals in the solvent completely and maintain the temperature at about 50° C. to 100° C. for over 2 hours. At 112 remove a part of the solvent at reduced pressure. In this example, about 30% to 80% of the solvent are removed. At 113 add deionized water to the solution to recrystallize the carotenoids. At 114 the products are filtered to obtain wet crystals of carotenoids.

At 115 the wet crystals are dried under vacuum to remove the residual solvents. At 116 highly purified carotenoids crystals are obtained.

EXAMPLE 1

260 g of potassium hydroxide is added into 2,160 ml of methanol solvent and stirred to dissolve completely. The alkaline solution is maintained at 35° to 40° C. 216 g of the commercially available marigold oleoresin and 2,880 ml of n-hexane are added into the alkaline solution. The mixture solution is stirred continuously and maintained at 35° to 40° C. for 3 hours or more to perform the saponification. After the saponification, crystals of lutein and zeaxanthin appeared in the solution. The crystals are collected using a simple suction filtration process. After the filtration, the collected lutein crystal is washed in deionized water until the filter is clear and chemically neutral. The wet crystal is dried in vacuum at 70° C. for 16 hours. Analyze the dried crystal and obtain the following results:

The total weight of the dried crystal: 12.0 g.

The total carotenoids contain: 99.9% ($^{1\%}E$=2550 in ethanol at 446 nm by UV/Vis spectrum), wherein 93.4% of the total carotenoids are lutein and 5.6% are zeaxanthin, as revealed by the HPLC analysis.

EXAMPLE 2

The steps of Example 1 are repeated, expect that the saponification is performed at the boiling point of alcohol mixture, about 65° C., for 1 hour. The dried crystals are analyzed and the following results are obtained:

The total weight of the dried crystal: 12.2 g.

The total carotenoids contain: 100.0% ($^{1\%}E$=2550 in ethanol at 446 nm by UV/Vis spectrum), wherein 92.6% of the total carotenoids are lutein and 4.9% are zeaxanthin, as measured by the HPLC analysis.

EXAMPLE 3

The steps of Example 1 are repeated, expect that 216 g of potassium hydroxide is used. After the process, the dried crystals are analysis to obtain the following results:

The total weight of the dried crystal: 12.1 g.

The total carotenoids contain: 99.5% ($^{1\%}E$=2550 in ethanol at 446 nm by UV/Vis spectrum), wherein 92.8% of the total carotenoids are lutein and 4.7% are zeaxanthin, as analyzed by the HPLC analysis.

EXAMPLE 4

The steps of Example 1 are repeated using the same recipe and the same saponification conditions. Thereafter, the mixture solution is diluted in 1,200 ml of deionized water. More precipitated lutein and zeaxanthin crystals are observed. The crystals are collected by filtration and washed in deionized water, as in Example 1. 15.5 g Crystals are obtained. Analyses show the total carotenoids contain in the products is 100.0%, as measured by UV/Vis, wherein 93.6% are lutein and 4.4% are zeaxanthin, as analyzed by the HPLC.

EXAMPLE 5

Hazardous Residual Solvent Reduced

The steps of Example 1 are repeated. After the lutein crystals produced are collected, the lutein crystals are washed with deionized water. The wet crystal is dissolved in 600 ml ketone and the solution is heated to 40° C. Reduce the air pressure of the system to 30 mmHg until 300 ml of the solvent are removed. After that, 1800 ml of deionized water are added to recrystallize the lutein and the zeaxanthin. The produced crystals are collected using a simple suction filtration process. The wet crystals are dried at the same conditions as example 1. The results show that the n-hexane and methanol solvent residuals in the obtained crystals are in the amounts of 6.3 to 50 ppm and <1 ppm (non-detectable), respectively. After proper treatment, the residual n-hexane solvent may be reduced to 1.0 to 1.6 ppm and the residual methanol solvent is non-detectable.

Effects of the Invention

The advantages of the present invention include the followings: First, in the present invention the saponification is performed efficiently under mild conditions. Another advantage of this invention is in its high carotenoids contain. In the embodiments of this invention, the total carotenoids contain is over 99%, as determined by the UV/Vis spectrophotometers, in which the lutein contain and the zeaxanthin contain are over 92% and lower than 6%, respectively, as determined by the HPLC analysis. No prior researches available have ever announced such high quality carotenoids (or lutein crystal) contains. In addition, in the invented method a large part of the organic solvents, i.e. more than 70%, used in the invented method can be recycled and reused. In the present invention the amount of the waste-washing water consumed is very small. Impacts to the environment may thus be prevented. Another advantage of this invention is the reduced amounts of the residual solvents. According to this invention more than 50% of the hazardous residual solvents may be removed from the carotenoids. Lutein in a higher quality and safe for human use is thus produced.

As the present invention has been shown and described with reference to preferred embodiments thereof, those skilled in the art will recognize that the above and other changes may be made therein without departing form the spirit and scope of the invention.

What is claimed is:

1. A method for the purification of carotenoids from plant extracts, comprising the steps of:
    (a) Saponifying a carotenoids-containing plant extract in a saponification solution containing at least one polar solvent and at least one nonpolar solvent at a reaction temperature which ranges from 10° C. to 65° C.;
    (b) Isolating the saponification reaction products containing carotnoids to obtain carotenoids crystals; and
    (c) Purifying the crystals by at least one method selected from the group consisting of heating, freezing and vacuum processing to obtain highly purified carotenoids.

2. The method according to claim 1, wherein said carotenoids-containing plant extract comprises at least one extract selected from the group consisting of the extract of broccoli, Brussels sprouts, cabbage, kale, spinach, green beans, lima beans, lettuce and marigold flower.

3. The method according to claim 2, wherein said carotenoids-containing plant extract comprises a marigold flower extract.

4. The method according to claim 1, wherein said saponification solution further comprises an alkali.

5. The method according to claim 4, wherein said alkali comprises at least one selected from the group consisting of potassium hydroxide and sodium hydroxide.

6. The method according to claim 1, wherein said polar solvent comprises an alcohol.

7. The method according to claim 6, wherein said alcohol comprises at least one selected from the group consisting of methanol, ethanol and propan-2-ol.

8. The method according to claim 1, wherein said polar solvent is methanol.

9. The method according to claim 1, wherein said nonpolar solvent comprises an aliphatic hydrocarbon solvent.

10. The method according to claim 9, wherein said aliphatic hydrocarbon solvent comprises at least one selected from the group consisting of hexane, pentane and heptane.

11. The method according to claim 1, wherein said nonpolar solvent is hexane.

12. The method according to claim 1, wherein the volume ratio of said polar solvent to said nonpolar solvent is from 1:3 to 3:1.

13. The method according to claim 4, wherein the weight ratio of said alkali to said carotenoids-containing plant extract is from 0.3 to 2.0.

14. The method according to claim 13, wherein the weight ratio of said alkali to said carotenoids-containing plant extract is 1.0 to 1.3.

15. The method according to claim 1, wherein reaction temperature of said saponification process ranges from 35° to 40° C.

16. The method according to claim 1, further comprising the step of diluting said saponified products with deionized water before isolating said carotenoids crystals from said saponified products.

17. The method according to claim 1, wherein said carotenoids crystals are isolated from said saponified products by filtration.

18. The method according to claim 17, wherein said carotenoids crystals are isolated from said saponified products by suction filtration.

19. The method according to claim 1, wherein said carotenoids crystals are purified by drying under vacuum condition.

20. The method according to claim 1, wherein said carotenoids crystals are purified by heating in the temperature of 50° to 100° C. under vacuum condition.

21. The method according to claim 1, further comprising the step of washing said crystals with deionized water after isolating said crystals from said saponification products.

22. The method according to claim 1, further comprising the steps of: dissolving said carotenoids-containing crystals in a water miscible solvent, removing parts of said solvent at reduced pressure, adding deionized water to recrystallize and filtering out said solution to obtain recrystalllized carotenoids-containing crystals, before said purification process.

23. The method according to claim 22, wherein said water miscible solvent comprises at least one selected from the group consisting of alcohol, ester and ketone.

24. The method according to claim 23, wherein said water miscible solvent is at least one selected from the group consisting of propan-2-ol, propan-1,2-diol, ethanol, ethyl acetate and acetone.

25. The method according to claim 22, wherein 30% to 80% of said solvent is removed before adding said deionized water.

26. The method according to claim 4, wherein said carotenoids-containing plant extract is marigold flower extract, said polar solvent is an alcohol, said nonpolar solvent is aliphatic hydrocarbon and said alkali comprises potassium hydroxide and sodium hydroxide.

27. The method according to claim 26 wherein the alcohol is methanol, said aliphatic hydrocarbon is n-hexane, said alkali is potassium hydroxide, the saponification reaction temperature is maintained at from 35 to 45 degrees C. for three hours to perform saponification and to precipitate crystal of lutein and zeaxanthin, separating the crystals from the reaction mixture by vacuum filtration and, washing the separated crystals with de-ionized water.

* * * * *